United States Patent [19]

Chiaramonte et al.

[11] Patent Number: 4,781,584
[45] Date of Patent: Nov. 1, 1988

[54] PROXIMAL RELEASE IMPRESSION TRAY

[76] Inventors: Vincent Chiaramonte, 75 Farmers Ave., Lindenhurst, N.Y. 11757; Richard Bernstein, 4 Dogwood Hill, Brookville, N.Y. 11545

[21] Appl. No.: 32,530

[22] Filed: Apr. 1, 1987

[51] Int. Cl.$^4$ ................................................ A01C 9/00
[52] U.S. Cl. ..................................................... 433/48
[58] Field of Search .................... 433/47, 45, 37, 63

[56] References Cited

U.S. PATENT DOCUMENTS 1,445,499  2/1923  Dougles ................................. 433/47
1,687,914  10/1928  Walder ................................. 433/47

FOREIGN PATENT DOCUMENTS 545545  7/1922  France .

Primary Examiner—Robert Peshock
Attorney, Agent, or Firm—James P. Malone

[57] ABSTRACT

Releasable dental impression tray has a top member, a side member and a handle. The tray has a compressible spring for compressing resilient impression material after it has set to facilitate removal of the tray.

1 Claim, 2 Drawing Sheets

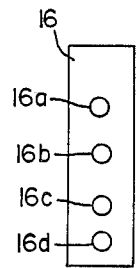
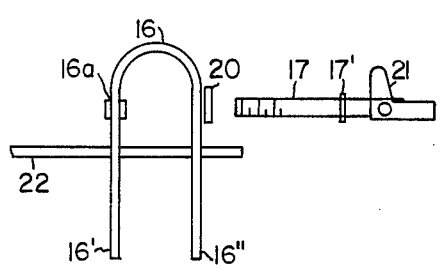
FIG.4B  FIG.4A
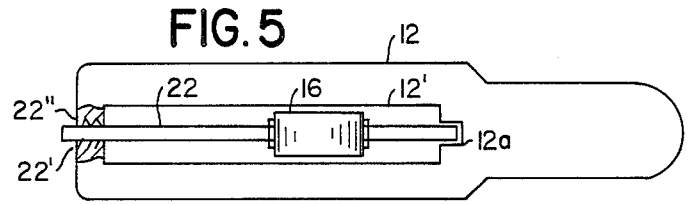
FIG.5
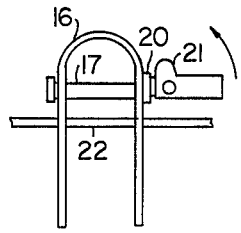
FIG.6
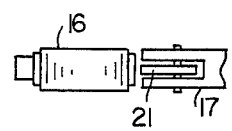
FIG.6A

PROXIMAL RELEASE IMPRESSION TRAY

TECHNICAL FIELD

This invention relates to dental trays for holding impression material for taking an impression of the patient's teeth and more particularly, to such means having means to compress resilient impression material.

PRIOR ART

The Prior art is shown in FIGS. 1 and 1A in this Application, as will be discussed.

THE INVENTION

The invention comprises releasable dental impression tray comprising: a dental tray having a top member, a side member and a handle connected to said members, the tray being adapted to hold resilient dental impression material, and means mounted on the tray for compressing the impression material after it has set.

OBJECTS OF THE INVENTION

Accordingly, a principal object of the invention is to provide new and improved tray means for making dental impressions.

Another object of the invention is to provide new and improved tray means for making dental impressions having means to compress resilient impression material in the tray.

Another object of the invention is to provide new and improved releasable dental impression tray comprising: a dental tray having a top member, a side member and a handle connected to said members, the tray being adapted to hold resilient dental impression material, and means mounted on the tray for compressing the impression material after it has set.

BRIEF DESCRIPTION OF THE DRAWINGS

These and other objects of the invention will be apparent from the following sepcification and drawings of which:

FIG. 1A is a side view illustrating the use of the covnentional impression tray of FIG. 1.

FIG. 4A is an exploded side of the compression spring and compressing screw FIG. 4B is a side view of FIG. 4A FIG. 5 is a top view of an embodiment of the invention.

FIGS. 6 and 6A are detail views showing the operation of the squeezing cam.

Figure 1:
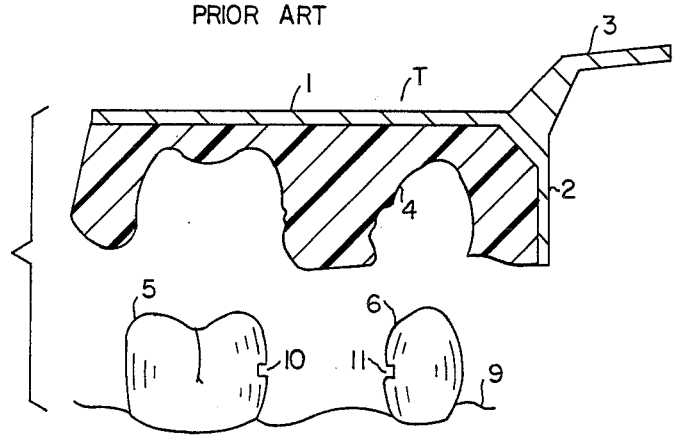
FIG. 1 is a side sectional view of a conventional impression tray of the prior art.

BEST MODE OF THE INVENTION:

Referring to the Figures, FIG. 1 shows a conventional impression tray T having a top member 1, a side member 2 and a handle 3. The impression material 4 is packed into the tray as shown. FIG. 1 shows a pair of teeth, 5 and 6, growing in gum 9, having grooves or other irregularities 7,8, cut into them. As a result of the grooves 7, 8, or other irregularities, when the tray is removed from the teeth 5 and 6, portions 10 and 11, of the impression material will be torn away.

Figure 2:
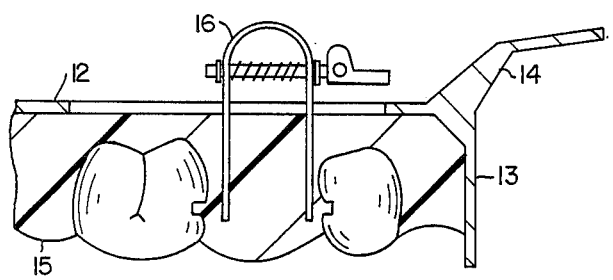
FIG. 2 is a side view partly in section of the present invention whrein the compression spring is relaxed.

FIG. 2 shows a side sectional view of the present invention having a top member 12, a side member 13, and a handle 14. The teeth 5', 5', have the same grooves or other irregularities 7', 8', as in FIG. 1A. In order to avoid the tearing of the impression material 15. Applicants provide a U shaped compressing spring 16. The impression material is resilient, for instance, rubber based.

The impression material is packed into the tray and around the teeth in conventional manner as shown in FIG. 2.

Figure 3:
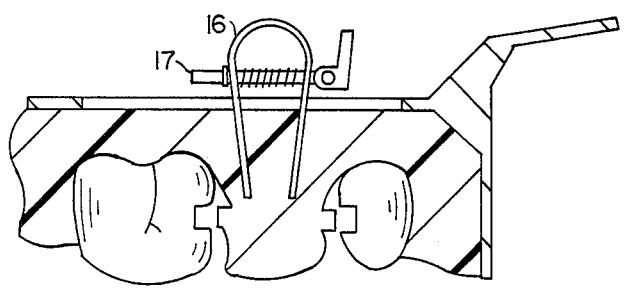
FIG. 3 is a side view partly in section wherein the compression spring is compressed

FIG. 3 shows the spring 16 having its ends compressed by the action of the comrpessing screw 17. Note that the resilient compression material 15 is now clear of the grooves 7', 8', so that the tray can be withdrawn without tearing away any impression material.

FIG. 4A shows a side view of the spring 16 assembly. The compression screw 17 has threads which engage the threaded member 18 and is tightened so that the shoulders 17' of the screw engage the washer 20. The cam lever 21 is then operated to compress together the ends 16', 16'' of the spring 16. A transverse rod 22 is mounted in the top member 12. The threads 22' engage the threads 22'' in the top member 12. The purpose of the transverse rod is to facilitate the positioning of the spring 16.

FIG. 4B shows a side view of the spring 16, having an aperture 16a, for the compressing screw, a second aperture 16b for the transverse rod and two apertures 16c, 16d, for retaining the impression material.

FIG. 5 shows a top view of our embodiment. The top 12 has a slot 12' through which the spring 16 is inserted. The top 12 has a shaftway 12a connecting with the slot 12' and a second threaded recess 22'' for the purpose of receiving the transverse rod 22. The purpose of the transverse rod 22 is to facilitate locating and holding the spring 16 in proper position for the particular impressions.

FIGS. 6 and 6A show details of the cam lock device 21. The compressing screw is threaded into the threaded shaftway 18 on the spring 16. Lever 21 is pivotally mounted on the screw 17. When the cam lever 21 is rotated up it will squeeze the open ends of the spring 16 together.

MODE OF OPERATION

1. The correct size spring is selected and placed into the slot on the tray.

2. The transverse rod is placed throught the threaded hole in the tray, through the hole in the spring and into the recess in the tray body. The screw is then tightened.

3. The U shaped spring is positioned by putting it at the desired part of the tray where the compression is needed.

4. With the lever 21 on the compressing screw in the released position, a mix of impression material is placed into the tray completely covering the spring assembly inside the tray.

5. The filled tray is placed into the mouth and allowed to set.

6. After the material has set, the lever on the com pressing screw is turned to the compressing position, compressing the rubber material away from the undercut areas and then the entire tray is lifted from the mouth in the standard way.

7. The lever is now released, relaxing the rubber so that it will fall back to its original shape.

8. The model is now ready to be poured by using either plaster, stone or equivalent.

9. After the stone has set, the lever is again returned to the compressing position and the model removed from the impression tray.

It is claimed:

1. Releasable dental impression tray comprising:

a dental tray having a top member having a slot, side member and a handle connected to said members, the tray being adapted to hold resilient dental impression material, and means mounted on the tray for compressing the impression material after it has set, wherein the means for compression is a U shaped spring mounted on the top member and extending through the slot and in the slot into the resilient impression material, and a screw means connected to move together the open ends of the U shaped spring member.

* * * * *